United States Patent [19]

Bebbington

[11] Patent Number: 5,658,759
[45] Date of Patent: Aug. 19, 1997

[54] RECOMBINANT DNA EXPRESSION VECTORS

[75] Inventor: Christopher Robert Bebbington, Windsor, United Kingdom

[73] Assignee: Celltech Limited, Berkshire, United Kingdom

[21] Appl. No.: 633,013

[22] Filed: Apr. 16, 1996

Related U.S. Application Data

[62] Division of Ser. No. 300,063, Sep. 2, 1994, Pat. No. 5,591,639, which is a continuation of Ser. No. 896,797, Jun. 9, 1992, abandoned, which is a continuation of Ser. No. 339,615, filed as PCT/GB88/00602, Jul. 22, 1988, abandoned.

[30] Foreign Application Priority Data

Jul. 23, 1987 [GB] United Kingdom .................. 8717430

[51] Int. Cl.$^6$ .................. C12N 15/00; C12N 5/00; C12P 21/06; C07H 21/04
[52] U.S. Cl. .................. 435/69.1; 435/172.3; 435/320.1; 435/325; 435/348; 435/419; 435/365.1; 435/358; 435/359; 435/360; 435/365; 536/24.1
[58] Field of Search .................. 435/32.01, 69.1, 435/172.3; 536/24.1

[56] References Cited

U.S. PATENT DOCUMENTS 4,769,326  9/1988  Rutter ......................................... 435/68

OTHER PUBLICATIONS

Whittle et al Prot Engin 1(6): 499, 1987.
Wong et al., "Human GM–CSF: Molecular Cloning of the Complementary DNA and Purification of the Natural and Recombinant Proteins", Science, v.228, pp. 810–815.
Simonsen et al., "Isolation and expression of an altered mouse dihydrofolate reductase cDNA", Proc. Natl. Acad. Sci. (USA), vol. 80, pp. 2495–2499, 1983.
Kaufman et al., "Amplification and Expression of Sequences Cotransfected with a Modular Dihydrofolate Reductase Complementary DNA Gene", J. Mol. Biol., v. 159 pp. 601–621, 1982.
Gething et al., "Cell–surface expression of influenza hemoagglutinin from a cloned DNA copy of the RNA gene", Nature, vol. 293, pp. 620–625, 1981.
McLean et al., "Cloning and expression of human lecithin–cholesterol acyltransferase cDNA", Proc. Natl. Acad. Sci. (USA), vol. 83, pp. 2335–2339, 1986.
Leonard et al., "Molecular cloning and expression of cDNAs for the human interleukin–2 receptor", Nature, vol. 311, pp. 626–631, 1984.

Foecking et al., "Powerful and versatile enhancer–promoter unit for mammalian expression vectors", Gene, 45 (1986) pp. 101–105.
Gray et al., "Expression of human immune interferon cDNA in E. coli and monkey cells", Nature, vol. 295, pp. 503–508, Feb., 1982.
Nunberg et al., "Live, Recombinant Vaccinia Virus Encoding Expression of the Feline Leukemia Virus Envelope Protein", Transcriptional Control Mecchanisms, (Abstract 0216), p. 154.
Treisman et al., "Transformation of rat cells by an altered polyoma virus genome expressing only the middle–T protein", Nature, vol. 292, pp. 292, pp. 595–600, 1981.
Boshart et al. In Sequence Specificity in Transcript and Translation pp. 511–520 "The Strong Enhancer Element In The Immediate Early Region of the Human Cytomegalovirus Genome", 1985.
Gruss et al. PNAs 76(9): 4317–4321 1979.
Hamer et al. Cell 17: 725–735 1979.
Mulligan et al. Nature 277: 108–114 1979.
F. Pasieau et al., "Growth hormone gene expression in eukaryotic cells directed by the Rous sarcoma virus long terminal repeat or cytomegalovirus immediate–early promoter" Gene, vol. 38, No. 1/3. pp. 227–232 1985.
R. R. Spaete et al., "Regulation of cytomegalovirus gene expression: α and β promoters are trans activated by viral functions in permissive human fibroblasts" Journal of Virology, vol. 56, No. 1, Oct. 1985, American Society for Microbiology (US) pp. 135–143.
J. A. Nelson et al., "Negative and Positive Regulation by a Short Segment in the 5'–Flanking Region of the Human Cytomegalovirus Major Immediate–Early Gene" Molecular and Cellular Biology, Nov. 1987, pp. 4125–4129 1987.
R. M. Stenberg et al., "Structural Analysis of the Major Immediate Early Gene of Human Cytomegalovirus" Journal of Virology, Jan. 1984, pp. 190–199 1984.

Primary Examiner—Suzanne E. Ziska
Attorney, Agent, or Firm—Spencer & Frank

[57] ABSTRACT

The invention provides expression vectors containing the promoter, enhancer and substantially complete 5'-untranslated region including the first intron of the major immediate early gene of human cytomegalovirus. Further vectors including the hCMV-MIE DNA linked directly to the coding sequence of a heterologous gene are described. Host cells transfected with the vectors and a process for producing heterologous polypeptides using the vectors and the use of the hCMV-MIE DNA for expression of a heterologous gene are also included within the invention.

10 Claims, 9 Drawing Sheets

```
                              T
       DNS            p       t                            AM
       sct            s       h                            fl
       aoy            t       3                            lu
       111            1       2                            31
        //                                                  /
       CCATGGTGTCAAGGACGGTGACTGCAGTGAATAATAAAATGTGTGTTTGTCCGAAATACG
  1    ---------+---------+---------+---------+---------+---------+  60
       GGTACCACAGTTCCTGCCACTGACGTCACTTATTATTTTACACACAAACAGGCTTTATGC CGTTTTGAGATTTCTGTCGCCGACTAAATTCATGTCGCGCGATAGTGGTGTTTATCGCCG
 61    ---------+---------+---------+---------+---------+---------+ 120
       GCAAAACTCTAAAGACAGCGGCTGATTTAAGTACAGCGCGCTATCACCACAAATAGCGGC C
                              l
                              a
                              1
       ATAGAGATGGCGATATTGGAAAAATCGATATTTGAAAATATGGCATATTGAAAATGTCGC
121    ---------+---------+---------+---------+---------+---------+ 180
       TATCTCTACCGCTATAACCTTTTTAGCTATAAACTTTTATACCGTATAACTTTTACAGCG E
                         c
                         o
                         R
                         V
       CGATGTGAGTTTCTGTGTAACTGATATCGCCATTTTTCCAAAAGTGATTTTTGGGCATAC
181    ---------+---------+---------+---------+---------+---------+ 240
       GCTACACTCAAAGACACATTGACTATAGCGGTAAAAAGGTTTTCACTAAAAACCCGTATG E
          c
          o
          R
          V
       GCGATATCTGGCGATAGCGGCTTATATCGTTTACGGGGGATGGCGATAGACGACTTTGGT
241    ---------+---------+---------+---------+---------+---------+ 300
       CGCTATAGACCGCTATCGCCGAATATAGCAAATGCCCCCTACCGCTATCTGCTGAAACCA GACTTGGGCGATTCTGTGTGTCGCAAATATCGCAGTTTCGATATAGGTGACAGACGATAT
301    ---------+---------+---------+---------+---------+---------+ 360
       CTGAACCCGCTAAGACACACAGCGTTTATAGCGTCAAAGCTATATCCACTGTCTGCTATA C BH      N   C
                                        f aa      s   l
                                        r le      i   a
                                        1 11          1
                                           /
       GAGGCTATATCGCCGATAGAGGCGACATCAAGCTGGCACATGGCCAATGCATATCGATCT
361    ---------+---------+---------+---------+---------+---------+ 420
       CTCCGATATAGCGGCTATCTCCGCTGTAGTTCGACCGTGTACCGGTTACGTATAGCTAGA
```

Fig. 4A

```
              S   C  BH
              s   f  aa
              p   r  le
              1   1  11
                     /
     ATACATTGAATCAATATTGGCCATTAGCCATATTATTCATTGGTTATATAGCATAAATCA
421  ---------+---------+---------+---------+---------+---------+ 480
     TATGTAACTTAGTTATAACCGGTAATCGGTATAATAAGTAACCAATATATCGTATTTAGT
      S        C  BH
      s        f  aa
      p        r  le
      1        1  11
                  /
     ATATTGGCTATTGGCCATTGCATACGTTGTATCCATATCATAATATGTACATTTATATTG
481  ---------+---------+---------+---------+---------+---------+ 540
     TATAACCGATAACCGGTAACGTATGCAACATAGGTATAGTATTATACATGTAAATATAAC

H
                     i         M              S
                     n         m              p
                     c         e              e
                     2         1              1
     GCTCATGTCCAACATTACCGCCATGTTGACATTGATTATTGACTAGTTATTAATAGTAAT
541  ---------+---------+---------+---------+---------+---------+ 600
     CGAGTACAGGTTGTAATGGCGGTACAACTGTAACTAATAACTGATCAATAATTATCATTA

CAATTACGGGGTCATTAGTTCATAGCCCATATATGGAGTTCCGCGTTACATAACTTACGG
601  ---------+---------+---------+---------+---------+---------+ 660
     GTTAATGCCCCAGTAATCAAGTATCGGGTATATACCTCAAGGCGCAATGTATTGAATGCC

B                                     A      A
              g                                     h      a
              l                                     a      t
              1                                     2      2
     TAAATGGCCCGCCTGGCTGACCGCCCAACGACCCCCGCCCATTGACGTCAATAATGACGT
661  ---------+---------+---------+---------+---------+---------+ 720
     ATTTACCGGGCGGACCGACTGGCGGGTTGCTGGGGGCGGGTAACTGCAGTTATTACTGCA

A     A
                                    h     a
                                    a     t
                                    2     2
     ATGTTCCCATAGTAACGCCAATAGGGACTTTCCATTGACGTCAATGGGTGGAGTATTTAC
721  ---------+---------+---------+---------+---------+---------+ 780
     TACAAGGGTATCATTGCGGTTATCCCTGAAAGGTAACTGCAGTTACCCACCTCATAAATG

B                         N
                    g                         d
                    l                         e
                    1                         1
     GGTAAACTGCCCACTTGGCAGTACATCAAGTGTATCATATGCCAAGTACGCCCCCTATTG
781  ---------+---------+---------+---------+---------+---------+ 840
     CCATTTGACGGGTGAACCGTCATGTAGTTCACATAGTATACGGTTCATGCGGGGGATAAC
```

Fig. 4B

```
      A   A                         B
      h   a                         g
      a   t                         l
      2   2                         1
     ACGTCAATGACGGTAAATGGCCCGCCTGGCATTATGCCCAGTACATGACCTTATGGGACT
841  ---------+---------+---------+---------+---------+---------+ 900
     TGCAGTTACTGCCATTTACCGGGCGGACCGTAATACGGGTCATGTACTGGAATACCCTGA

S
                   n
                   a                               D N S
                   B                               s c t
                   1                               a o y
                                                   1 1 1
                                                    //
     TTCCTACTTGGCAGTACATCTACGTATTAGTCATCGCTATTACCATGGTGATGCGGTTTT
901  ---------+---------+---------+---------+---------+---------+ 960
     AAGGATGAACCGTCATGTAGATGCATAATCAGTAGCGATAATGGTACCACTACGCCAAAA

GGCAGTACATCAATGGGCGTGGATAGCGGTTTGACTCACGGGGATTTCCAAGTCTCCACC
961  ---------+---------+---------+---------+---------+---------+ 1020
     CCGTCATGTAGTTACCCGCACCTATCGCCAAACTGAGTGCCCCTAAAGGTTCAGAGGTGG

A   A                         B
           h   a                         a
           a   t                         n
           2   2                         1
      CCATTGACGTCAATGGGAGTTTGTTTTGGCACCAAAATCAACGGGACTTTCCAAAATGTC
1021  ---------+---------+---------+---------+---------+---------+ 1080
      GGTAACTGCAGTTACCCTCAAACAAAACCGTGGTTTTAGTTGCCCTGAAAGGTTTTACAG

GTAACAACTCCGCCCCATTGACGCAAATGGGCGGTAGGCGTGTACGGTGGGAGGTCTATA
1081  ---------+---------+---------+---------+---------+---------+ 1140
      CATTGTTGAGGCGGGGTAACTGCGTTTACCCGCCATCCGCACATGCCACCCTCCAGATAT

B H
                 B s s S                      G   A
                 a p i a                      s   h
                 n 1 A c                      u   a
                 2 2 1 1                      1   2
                  ///
      TAAGCAGAGCTCGTTTAGTGAACCGTCAGATCGCCTGGAGACGCCATCCACGCTGTTTTG
1141  ---------+---------+---------+---------+---------+---------+ 1200
      ATTCGTCTCGAGCAAATCACTTGGCAGTCTAGCGGACCTCTGCGGTAGGTGCGACAAAAC

N
                      B                    D   B C G s S X
                      b                    s   g f d p a m
                      v                    a   l r i B c a
                      2                    1   1 1 2 2 2 3
                                                 ////
      ACCTCCATAGAAGACACCGGGACCGATCCAGCCTCCGCGGCCGGGAACGGTGCATTGGAA
1201  ---------+---------+---------+---------+---------+---------+ 1260
      TGGAGGTATCTTCTGTGGCCCTGGCTAGGTCGGAGGCGCCGGCCCTTGCCACGTAACCTT
```

Fig. 4C

```
         CGCGGATTCCCCGTGCCAAGAGTGACGTAAGTACCGCCTATAGAGTCTATAGGCCCACCC
    1261 ---------+---------+---------+---------+---------+---------+ 1320
         GCGCCTAAGGGGCACGGTTCTCACTGCATTCATGGCGGATATCTCAGATATCCGGGTGGG

B                   N
         S s                 N  s S
         t t                 s  p p
         y X                 i  H h
         1 1                 1  1 1
                                /
         CCTTGGCTTCTTATGCATGCTATACTGTTTTTGGCTTGGGGTCTATACACCCCCGCTTCC
    1321 ---------+---------+---------+---------+---------+---------+ 1380
         GGAACCGAAGAATACGTACGATATGACAAAAACCGAACCCCAGATATGTGGGGGCGAAGG

E
                                   s
                                   p
                                   1
         TCATGTTATAGGTGATGGTATAGCTTAGCCTATAGGTGTGGGTTATTGACCATTATTGAC
    1381 ---------+---------+---------+---------+---------+---------+ 1440
         AGTACAATATCCACTACCATATCGAATCGGATATCCACACCCAATAACTGGTAATAACTG

P
                                                   f
                                                   l
                                                   M
                                                   1
         CACTCCCCTATTGGTGACGATACTTTCCATTACTAATCCATAACATGGCTCTTTGCCACA
    1441 ---------+---------+---------+---------+---------+---------+ 1500
         GTGAGGGGATAACCACTGCTATGAAAGGTAATGATTAGGTATTGTACCGAGAAACGGTGT

E
                          c
                          o
                          5
                          7
         ACTCTCTTTATTGGCTATATGCCAATACACTGTCCTTCAGAGACTGACACGGACTCTGTA
    1501 ---------+---------+---------+---------+---------+---------+ 1560
         TGAGAGAAATAACCGATATACGGTTATGTGACAGGAAGTCTCTGACTGTGCCTGAGACAT

E
                         c
                         o
                         3
                         1
         TTTTTACAGGATGGGGTCTCATTTATTATTTACAAATTCACATATACAACACCACCGTCC
    1561 ---------+---------+---------+---------+---------+---------+ 1620
         AAAAATGTCCTACCCCAGAGTAAATAATAAATGTTTAAGTGTATATGTTGTGGTGGCAGG

B
         s
         p                              X           A           A
         1                              h           v           f
         2                              o           a           1
                                        2           1           3
         CCAGTGCCCGCAGTTTTTATTAAACATAACGTGGGATCTCCACGCGAATCTCGGGTACGT
    1621 ---------+---------+---------+---------+---------+---------+ 1680
         GGTCACGGGCGTCAAAAATAATTTGTATTGCACCCTAGAGGTGCGCTTAGAGCCCATGCA
```

Fig. 4D

```
           B                    B                                       B
           s                    Bs                                      Bs
           p                    ap                                      ap
           M                    n1                                      n1
           2                    22                                      22
                                 /                                       /
       GTTCCGGACATGGGCTCTTCTCCGGTAGCGGCGGAGCTTCTACATCCGAGCCCTGCTCCC
  1681---------+---------+---------+---------+---------+---------+ 1740
       CAAGGCCTGTACCCGAGAAGAGGCCATCGCCGCCTCGAAGATGTAGGCTCGGGACGAGGG

G                                              H
                    s                                              a
                    u                                              e
                    1                                              1
       ATGCCTCCAGCGACTCATGGTCGCTCGGCAGCTCCTTGCTCCTAACAGTGGAGGCCAGAC
  1741---------+---------+---------+---------+---------+---------+ 1800
       TACGGAGGTCGCTGAGTACCAGCGAGCCGTCGAGGAACGAGGATTGTCACCTCCGGTCTG

D
                                             s
                                             a
                                             1
       TTAGGCACAGCACGATGCCCACCACCACCAGTGTGCCGCACAAGGCCGTGGCGGTAGGGT
  1801---------+---------+---------+---------+---------+---------+ 1860
       AATCCGTGTCGTGCTACGGGTGGTGGTGGTCACACGGCGTGTTCCGGCACCGCCATCCCA

BH                        N
                   ABsgS                     s                    A B
                   vapia                     p                    f b
                    an1Ac                    B                    l v
                    12211                    2                    2 2
                     ///
       ATGTGTCTGAAAATGAGCTCGGGGAGCGGGCTTGCACCGCTGACGCATTTGGAAGACTTA
  1861---------+---------+---------+---------+---------+---------+ 1920
       TACACAGACTTTTACTCGAGCCCCTCGCCCGAACGTGGCGACTGCGTAAACCTTCTGAAT N                     N
             s                     sP
             p                     pv
             B                     Bu
             2                     22
                                    /
       AGGCAGCGGCAGAAGAAGATGCAGGCAGCTGAGTTGTTGTGTTCTGATAAGAGTCAGAGG
  1921---------+---------+---------+---------+---------+---------+ 1980
       TCCGTCGCCGTCTTCTTCTACGTCCGTCGACTCAACAACACAAGACTATTCTCAGTCTCC H
                       iH
                       np
                       ca                                        S
                       21                                        c
                                                                 a
                        /                                        1
       TAACTCCCGTTGCGGTGCTGTTAACGGTGGAGGGCAGTGTAGTCTGAGCAGTACTCGTTS
  1981---------+---------+---------+---------+---------+---------+ 2040
       ATTGAGGGCAACGCCACGACAATTGCCACCTCCCGTCACATCAGACTCGTCATGAGCAAC
```

Fig. 4E

```
                    B B
                    s s
                    s s                                          DNS
                    H H                                          sct
                    2 2                                          aoy
                                                                 111
                                                                  //
       CTGCCGCGCGCGCCACCAGACATAATAGCTGACAGACTAACAGACTGTTCCTTTCCATGG
  2041---------+---------+---------+---------+---------+---------+ 2100
       GACGGCGCGCGCGGTGGTCTGTATTATCGACTGTCTGATTGTCTGACAAGGAAAGGTACC P                    DNS
                    s                    sct
                    t                    aoy
                    1                    111
                                          //  NcoI
       GTCTTTTCTGCAGTCACCGTCCTTGACACCATG
  2101---------+---------+---------+
       CAGAAAAGACGTCAGTGGCAGGAACTGTG
```

INSERT HCMV PROMOTER FRAGMENT IN THE HIND3 SITE OF EE6
Mismatch: 0  MinCuts = 1  MaxCuts: 3

RECOMBINANT DNA EXPRESSION VECTORS

This is a Division of application Ser. 08/300,063, filed Sep. 02, 1994; which is a Continuation of 07/896,797, filed Jun. 9, 1992 now abandoned which is a Continuation of 07/339,615, filed as PCT/GB88/00602, Jul. 22, 1988, now abandoned.

FIELD OF THE INVENTION

This invention relates to expression vectors containing a DNA sequence from the human cytomegalovirus major immediate early gene, to host cells containing such vectors, to a method of producing a desired polypeptide by using vectors containing said sequence and to the use of said DNA sequence.

BACKGROUND OF THE INVENTION

The main aim of workers in the field of recombinant DNA technology is to achieve as high a level of production as possible of a particular polypeptide. This is particularly true of commercial organisations who wish to exploit the use of recombinant DNA technology to produce polypeptides which naturally are not very abundant.

Generally the application of DNA technology involves the cloning of a gene encoding the desired polypeptide, placing the cloned gene in a suitable expression vector, transfecting a host cell line with the vector, and culturing the transferred cell line to produce the polypeptide. It is almost impossible to predict whether any particular vector or cell line or combination thereof will lead to a useful level of production.

In general, the factors which significantly affect the amount of polypeptide produced by a transferred cell line are: 1. gene copy number, 2. efficiency with which the gene is transcribed and the mRNA translated, 3. the stability of the mRNA and 4. the efficiency of secretion of the protein.

The majority of work directed at increasing expression levels of recombinant polypeptides has focussed on improving transcription initiation mechanisms. As a result the factors affecting efficient translation are much less well understood and defined, and generally it is not possible to predict whether any particular DNA sequences will be of use in obtaining efficient translation.

Attempts at investigating translation have consisted largely of varying the DNA sequence around the consensus translation start signal to determine what effect this has on translation initiation (Kozak M. Cell 41 283–292 (1986)).

Studies involving expression of desired heterologous genes normally use both the coding sequence and at least part of the 5'-untranslated sequence of the heterologous gene such that translation initiation is from the natural sequence of the gene. This approach has been found to be unreliable probably as a result of the hybrid nature of the 5'-untranslated region and the fact that the presence of particular 5-untranslated sequences can lead to poor initiation of translation (Kozak H. Procl. Natl. Acad. Sci. 83 2850–2854 (1986) and Pelletier and Sonenberg Cell 40 515–526 (1985)). This variation in translation has a detrimental effect on the amount of the product produced.

Previous studies (Boshart et al Cell 41 521–530 (1985) and Pasleau et al, Gene 38 227–232 (1985); Stenberg et al, J. Virol 49 (1) 190–199 (1984); Thomsen et al Proc. Natl. Acad. Sci. USA 81 659–663 (1984) and Foecking and Hofstetter Gene 45 101–105 (1986)) have used sequences from the upstream region of the hCMV-MIE gene in expression vectors. These have, however, solely been concerned with the use of the sequences as promoters and/or enhancers. Spaete and Mocarski (J. Virol 56 (1) 135–143, 1985) have used a PstI to PstI fragment of the hCMV-MIE gene encompassing the promoter, enhancer and part of the 5'-untranslated region, as a promoter for expression of heterologous genes. In order to obtain translation the natural 5'-untranslated region of the heterologous gene was used.

In published European Patent Application No. 260148, a method for the continuous production of a heterologous protein is described. The expression vectors constructed contain part of the 5'-untranslated region of the hCMV-MIE gene as a stabilising sequence. The stabilising sequence is placed in the 5'-untranslated region of the gene encoding the desired heterologous protein i.e. the teaching is again that the natural 5'-untranslated region of the gene is essential for translation.

SUMMARY OF THE INVENTION

In a first aspect the invention provides a vector containing a DNA sequence comprising the promoter, enhancer and substantially complete 5'-untranslated region including the first intron of the major immediate early gene of human cytomegalovirus.

In a preferred embodiment of the first aspect of the invention, the vector includes a restriction site for insertion of a heterologous gene.

The present invention is based on the discovery that vectors containing a DNA sequence comprising the promoter, enhancer and complete 5'-untranslated region of the major or immediate early gene of the human cytomegalovirus (hCMV-MIE) upstream of a heterologous gene result in high level expression of the heterologous gene product. In particular, we have unexpectedly found that when the hCMV-MIE derived DNA is linked directly to the coding sequence of the heterologous gene high levels of mRNA translation are achieved. This efficient translation of mRNA is achieved consistently and appears to be independent of the particular heterologous gene being expressed.

In a second aspect the invention provides a vector containing a DNA sequence comprising the promoter, enhancer and substantially complete 5'-untranslated region including the first intron of the major immediate early gene of human cytomegalovirus upstream of a heterologous gene.

The hCMV-MIE derived DNA according to the second aspect of the invention may be separated from the coding sequence of the heterologous gene by intervening DNA such as for example by the 5'-untranslated region of the heterologous gene. Advantageously the hCMV-MIE derived DNA may be linked directly to the coding sequence of the heterologous gene.

In a preferred embodiment of the second aspect of the invention, the invention provides a vector containing a DNA sequence comprising the promoter, enhancer and substantially complete 5'-untranslated region including the first intron of the hCMV-MIE gene linked directly to the DNA coding sequence of the heterologous gene.

Preferably the hCMV-MIE derived sequence includes a sequence identical to the natural hCMV-MIE translation initiation signal. It may however be necessary or convenient to modify the natural translation initiation signal to facilitate linking the coding sequence of the desired polypeptide to the hCMV-MIE sequence, i.e. by introducing a convenient restriction enzyme recognition site. For example the translation initiation site may advantageously be modified to provide an NcoI recognition site.

The heterologous gene may be a gene coding for any eukaryotic polypeptide such as for example a mammalian polypeptide such as an enzyme, e.g. chymosin or gastric lipase; an enzyme inhibitor, e.g. tissue inhibitor of metalloproteinase (TIMP); a hormone, e.g. growth hormone; a lymphokine, e.g. an interferon; a plasminogen activator, e.g. tissue plasminogen activator (tPA) or prourokinase; or a natural, modified or chimeric immunoglobulin or a fragment thereof including chimeric immunoglobulins having dual activity such as antibody-enzyme or antibody-toxin chimeras.

According to a third aspect of the invention there is provided host cells transfected with vectors according to the first or second aspect of the invention.

The host cell may be any eukaryotic cell such as for example plant, or insect cells but is preferably a mammalian cell such as for example CHO cells or cells of myeloid origin e.g. myeloma or hybridoma cells.

In a fourth aspect the invention provides a process for the production of a heterologous polypeptide by culturing a transferred cell according to the third aspect of the invention.

In a fifth aspect the invention provides the use of a DNA sequence comprising the promoter, enhancer and substantially complete 5'-untranslated region including the first intron of the hCMV-MIE gene for expression a heterologous gene.

In a preferred embodiment of the fifth aspect of the invention the hCMV-HIE derived DNA sequence is linked directly to the DNA coding sequence of the heterologous gene.

Also included within the scope of the invention are plasmids pCMGS, pHT.1 and pEE6hCMV.

BRIEF DESCRIPTION OF THE DRAWINGS

The present invention is now described, by way of example only, with reference to the accompanying drawings in which.

DETAILED DESCRIPTION OF THE EMBODIMENTS

EXAMPLE 1

The Pst-lm fragment of hCMV (Boshart et al Cell 41 521–530 (1985) Spaete & Mocarski J. Virol 56 (1) 135–143 (1985)) contains the promoter-enhancer and most of the 5'-untranslated leader of the MIE gene including the first intron. The remainder of the 5'untranslated sequence can be recreated by attaching a small additional sequence of approximately 20 base pairs.

Many eukaryotic genes contain an NcoI restriction site (5'-CCATGG-3') overlapping the translation start site, since this sequence frequently forms part of a preferred translation initiation signal 5'ACCATGPu-3'. The hCMV-MIE gene does not have an NcoI site at the beginning of the protein coding sequence but a single base-pair alteration causes the sequence both to resemble more closely the "Kozak" concensus initiation signal and introduces an NcoI recognition site. Therefore a pair of complementary oligonucleotides were synthesised of the sequence:

```
GTCACCGTCCTTGACAC
|||||||||||||||||
ACGTCAGTGGCAGGAACTGTGGTAC
``` which when fused to the Pst-lm fragment of hCMV will recreate the complete 5'-untranslated sequence of the MIE gene with the single alteration of a G to a C at position −1 relative to the translation initiation codon.

Figure 3:
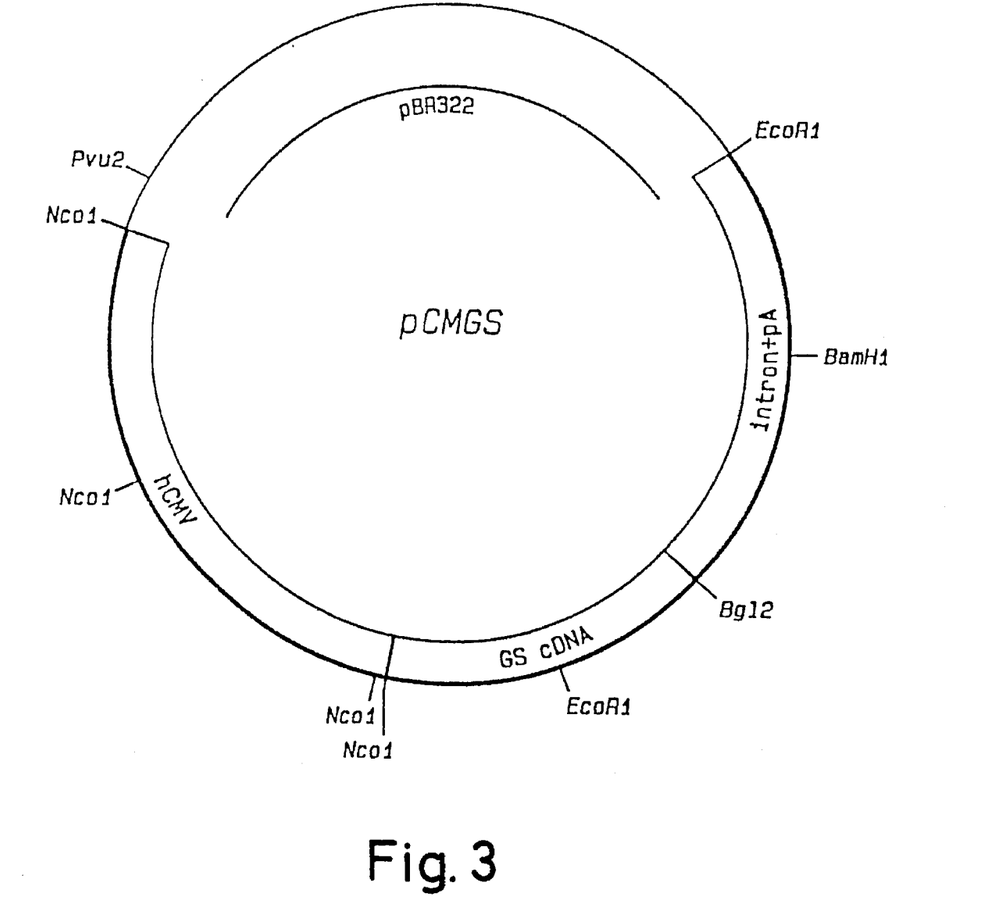
FIG. 3: shows a diagrammatic representation of plasmid pCMGS
Figure 4A:
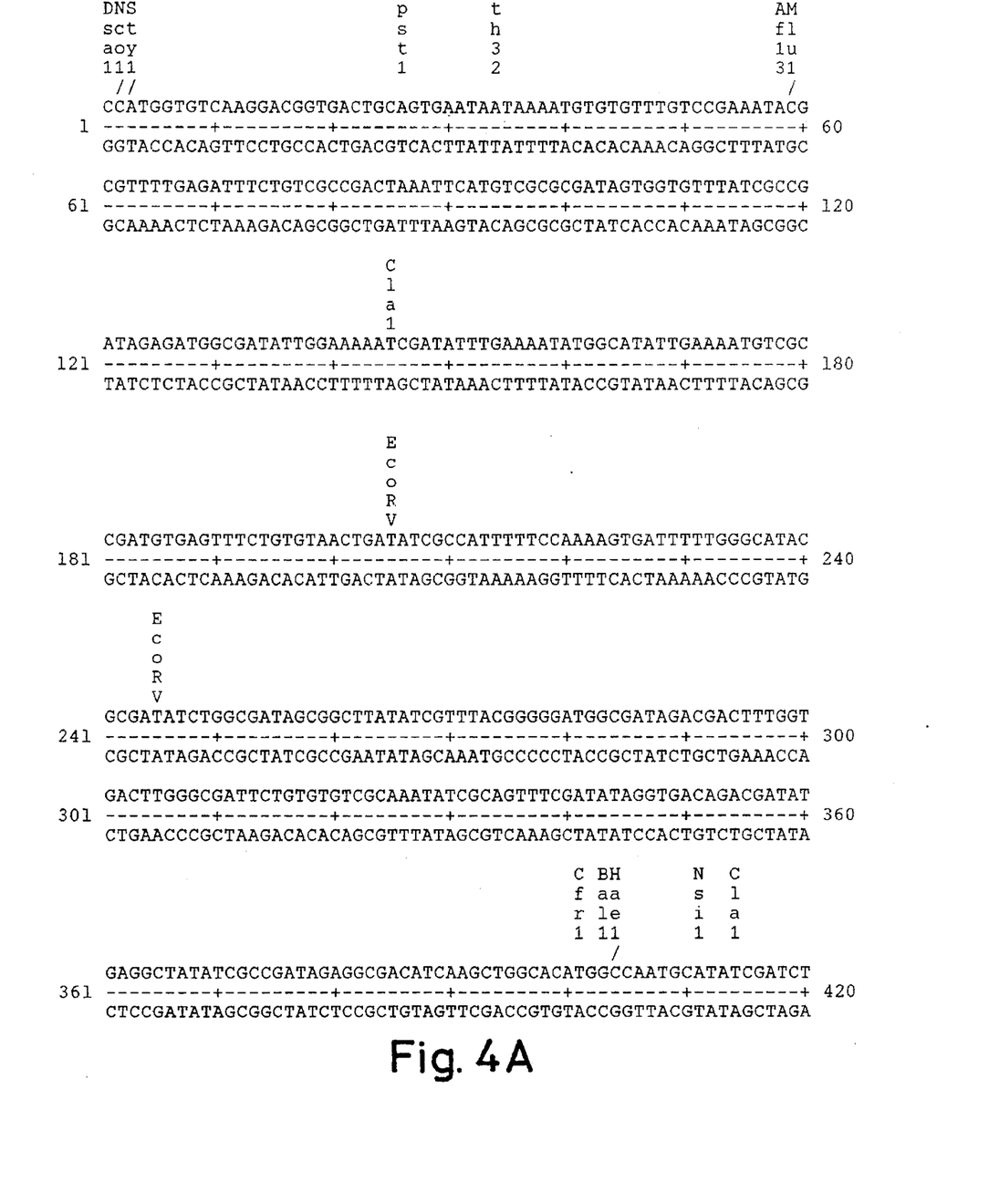
FIG. 4: shows the complete sequence of the promoter-enhancer hCMV-MIE including both the first intron and a modified translation 'start' site
Figure 4B:
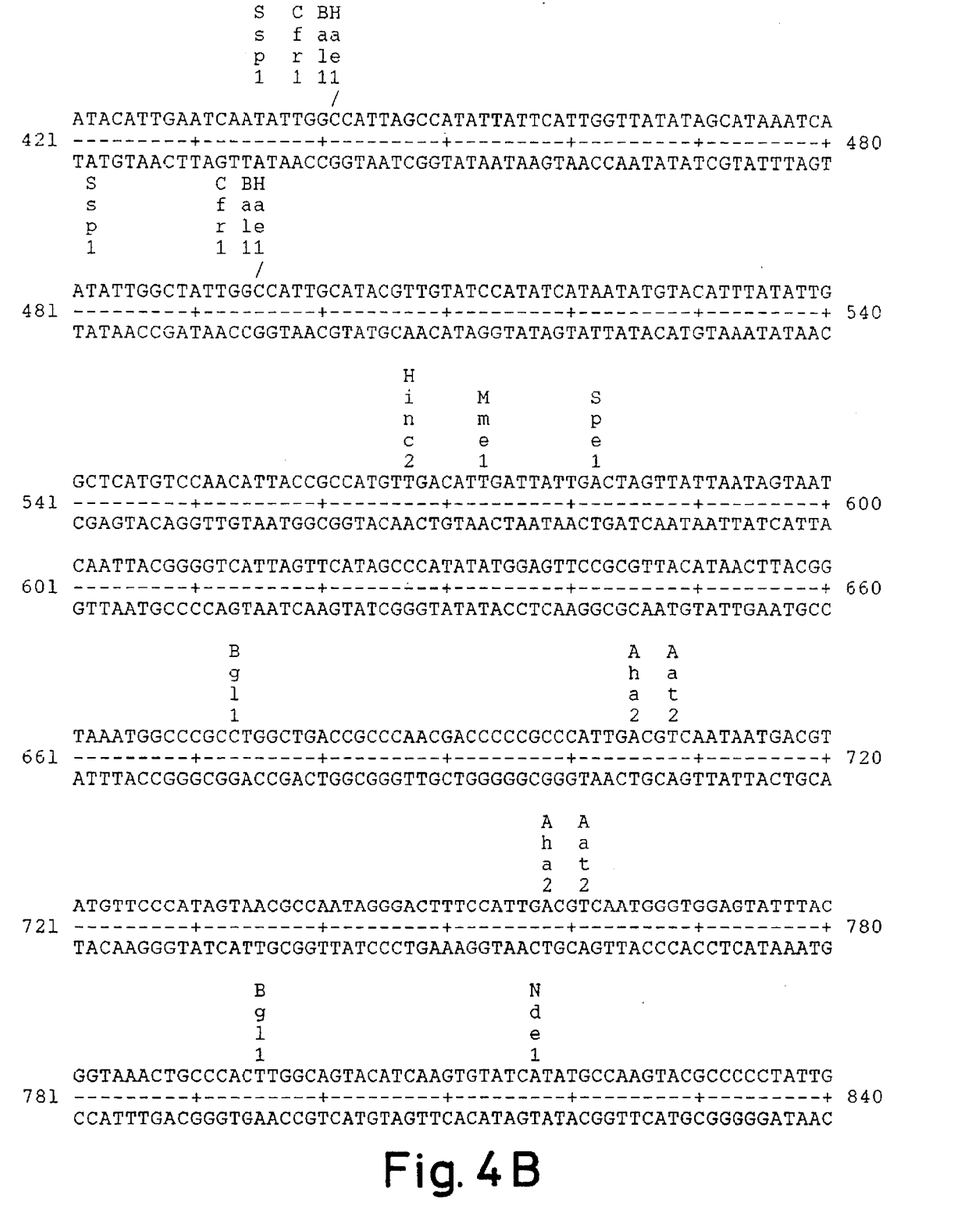
Figure 4C:
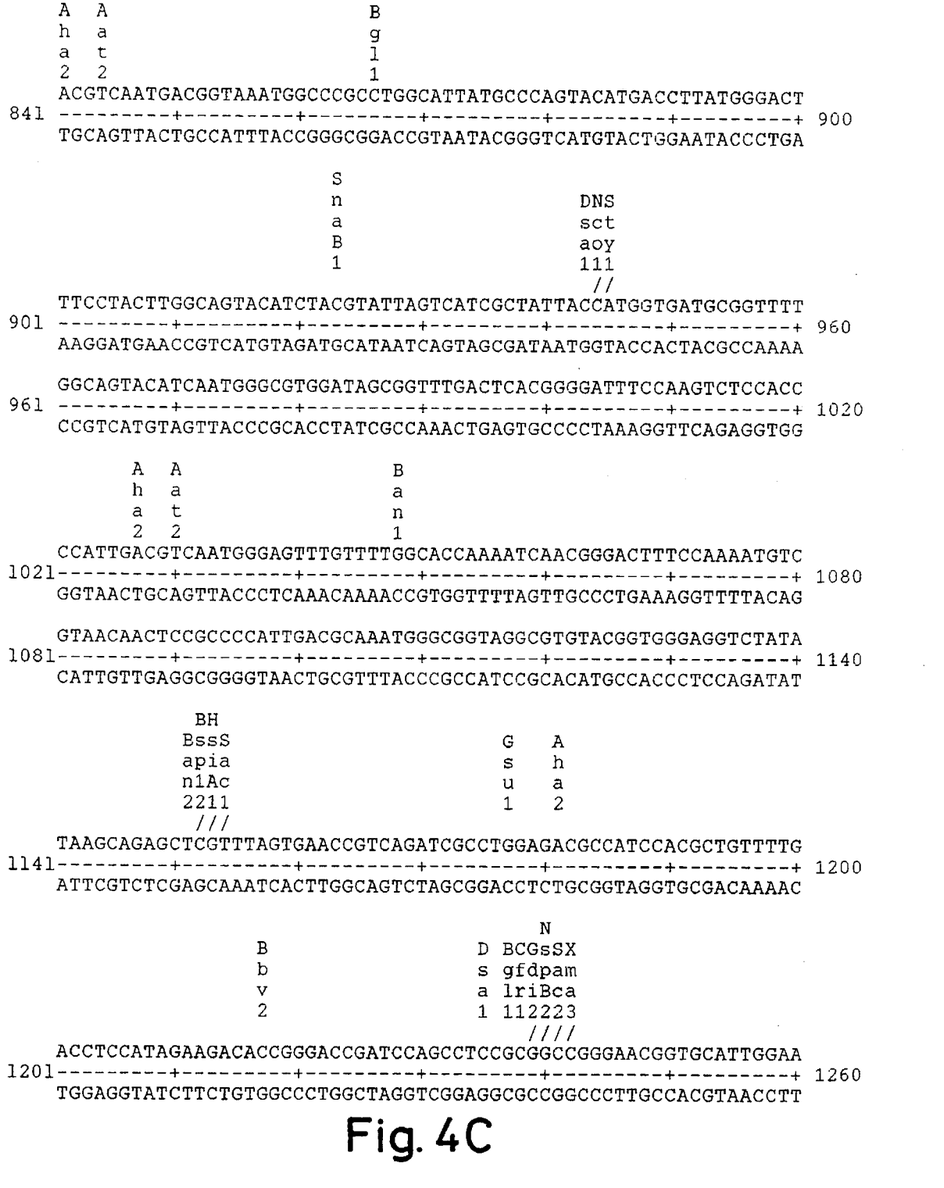
Figure 4D:
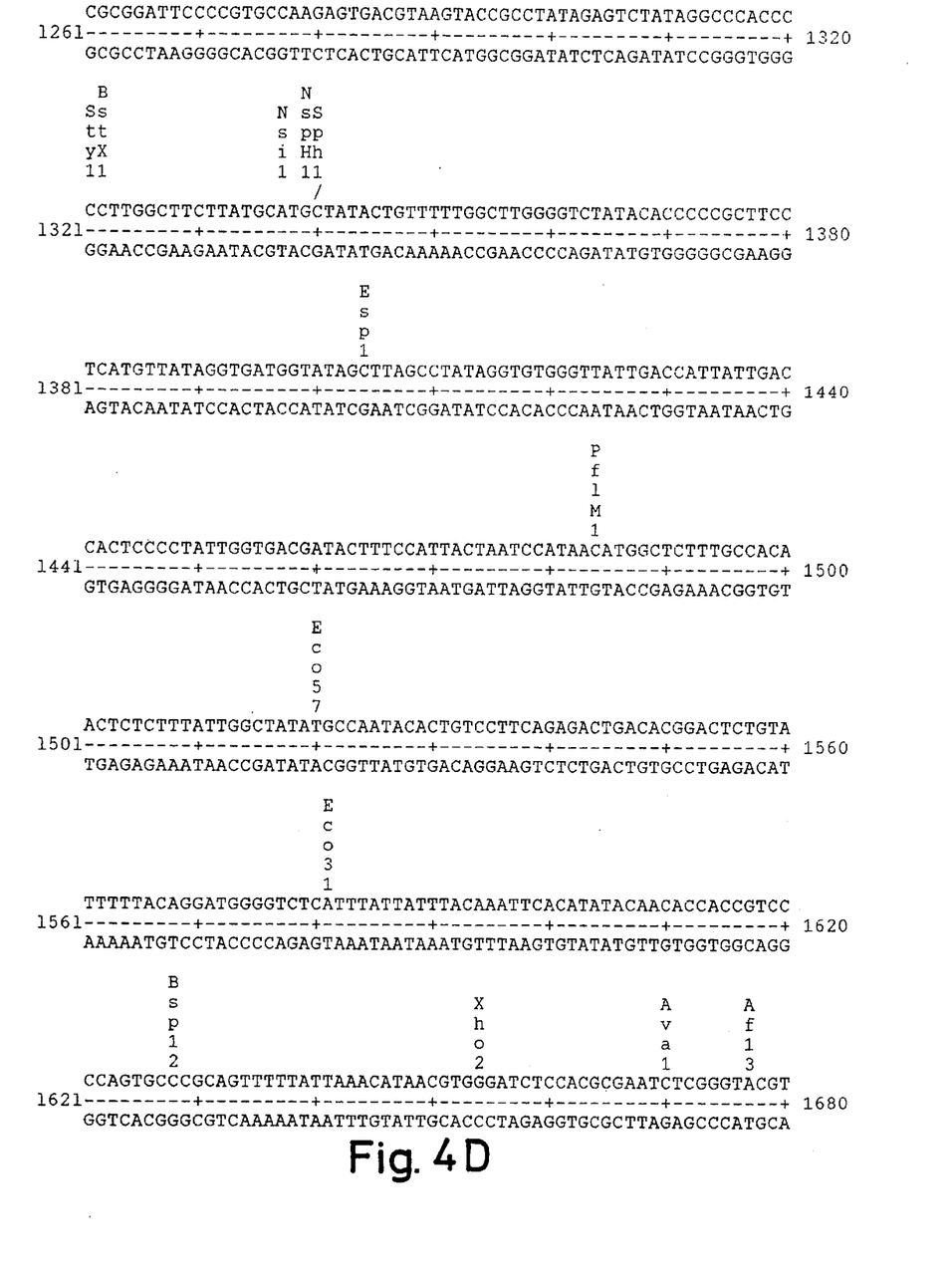
Figure 4E:
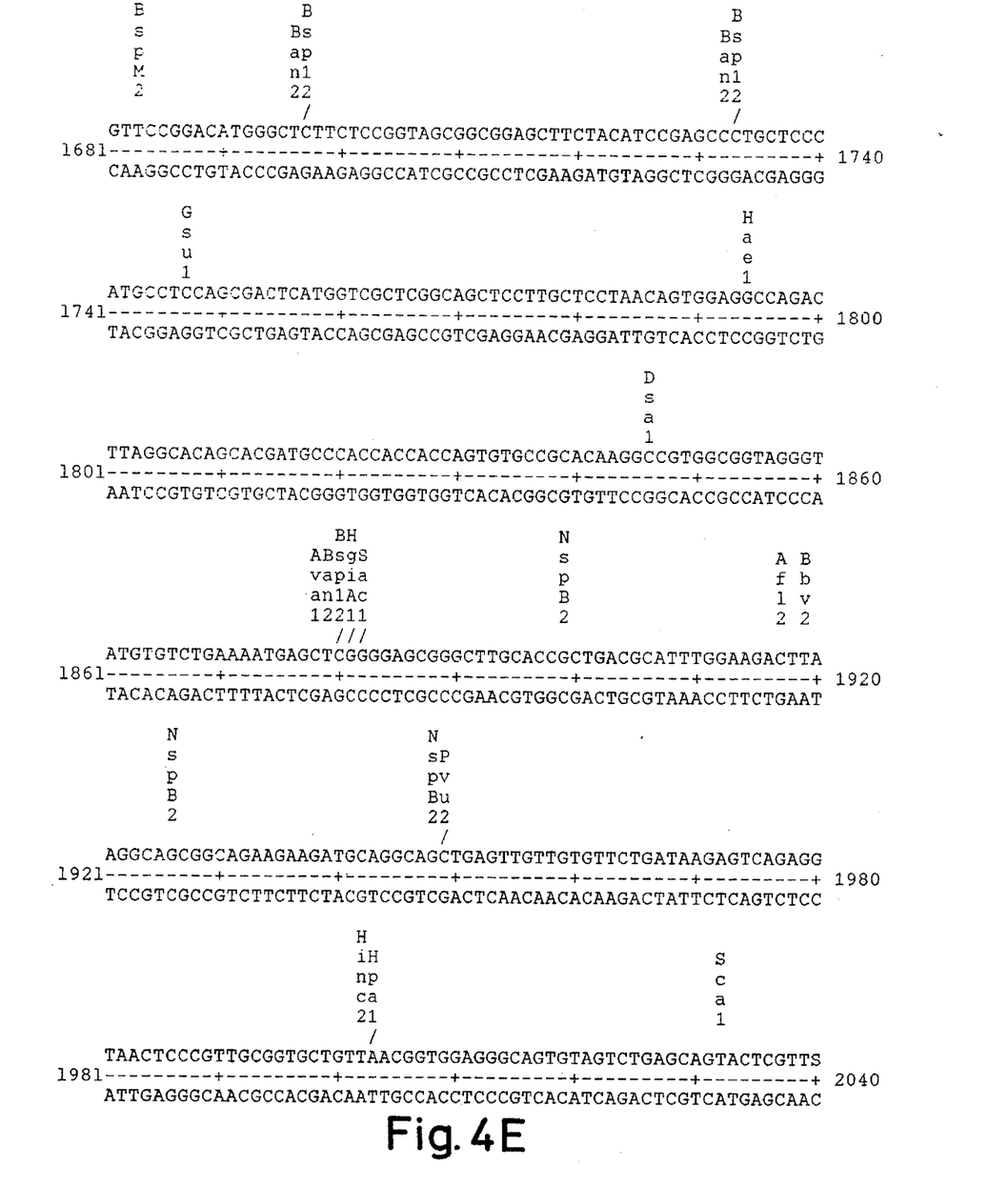
Figure 4F:
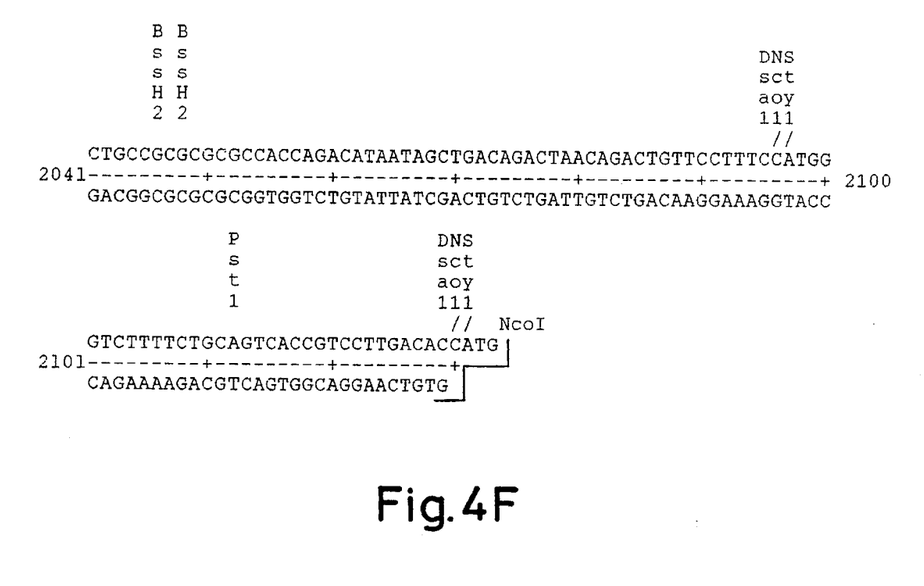
Figure 5:
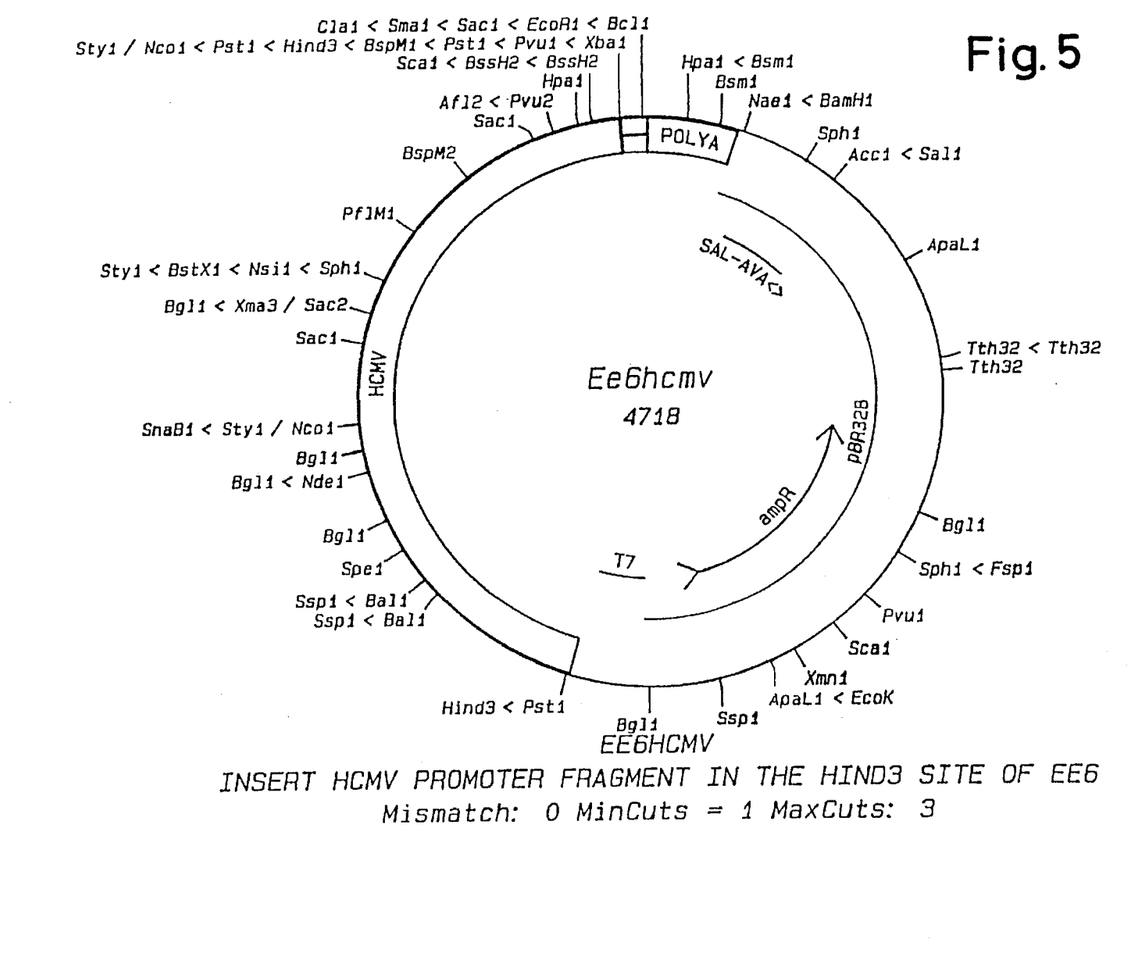
FIG. 5: shows a diagrammatic representation of plasmid pEE6.hCMV

This synthetic DNA fragment was introduced between the hCMV Pst-lm promoter-enhancer leader fragment and a glutamine synthetase (GS) coding sequence by ligation of the Pst-lm fragment and the synthetic oligomer with NcoI digested pSV2.GS to generate a new plasmid, pCMGS (The production of pSV2.GS is described in published International Patent Application No. WO 8704462). pCMGS is shown in FIG. 3. pCMGS thus contains a hybrid transcription unit consisting of the following: the synthetic oligomer described above upstream of the hCMV-MIE promoter-enhancer (where it serves merely as a convenient PatI - NcoI "adaptor"), the hCMV-MIE promoter and the complete 5' untranslated region of the MIE gene, including the first intron, fused directly to the GS coding sequence at the translation initiation site.

pCMGS was introduced into CHO-KI cells by calcium phosphate mediated transfection and the plasmid was tested for the ability to confer resistance to the GS-inhibitor methionine sulphoximine (MSX). The results of a comparison with pSV2.GS are shown in Table 1.

It is clear that pCMGS can confer resistance to 20M MSX at a similar frequency to pSV2.GS, demonstrating that active GS enzyme indeed expressed in this vector.

TABLE 1

Results of transfection of GS-expression vectors into CHO-KI cells

| Vector | no. colonies/$10^6$ cells resistant to 20 μM MSX |
| --- | --- |
| pSV2.GS | 32 |
| PCMGS | 17 |
| Control | 0 |

EXAMPLE 2

The TIMP cDNA and SV40 polyadenylation signal as used in pTIMP 1 Docherty et al (1985) Nature 318, 66–69, was inserted into pEE6 between the unique HindIII and BamHI sites to create pEE6TIMP. pEE6 is a bacterial vector from which sequences inhibitory to replication in mammalian cells have been removed. It contains the XmnI to BclI portion of pCT54 (Emtage et al 1983 Proc. Natl. Aced. Sci. USA 80, 3671–3675) with a pSP64 (Melton et al 1984: Nucleic Acids. Res. 12, 7035) polylinker inserted in between the HindIII and EcoRI sites. The BamHI and SalI sites have been removed from the polylinker by digestion, filling in with Klenow enzyme and religation. The BclI to BamHI fragment is a 237 bp SV40 early polyadenylation signal (SV40 2770 to 2533). The BamHI to the BglI fragment is derived from pBR328 (375 to 2422) with an additional deletion between the SalI and the AvaI sites (651 to 1425)

following the addition of a SalI linker to the AvaI site. The sequence from the BglII to the XmnI site originates from the β-lactamase gene of pSP64.

Figure 2:
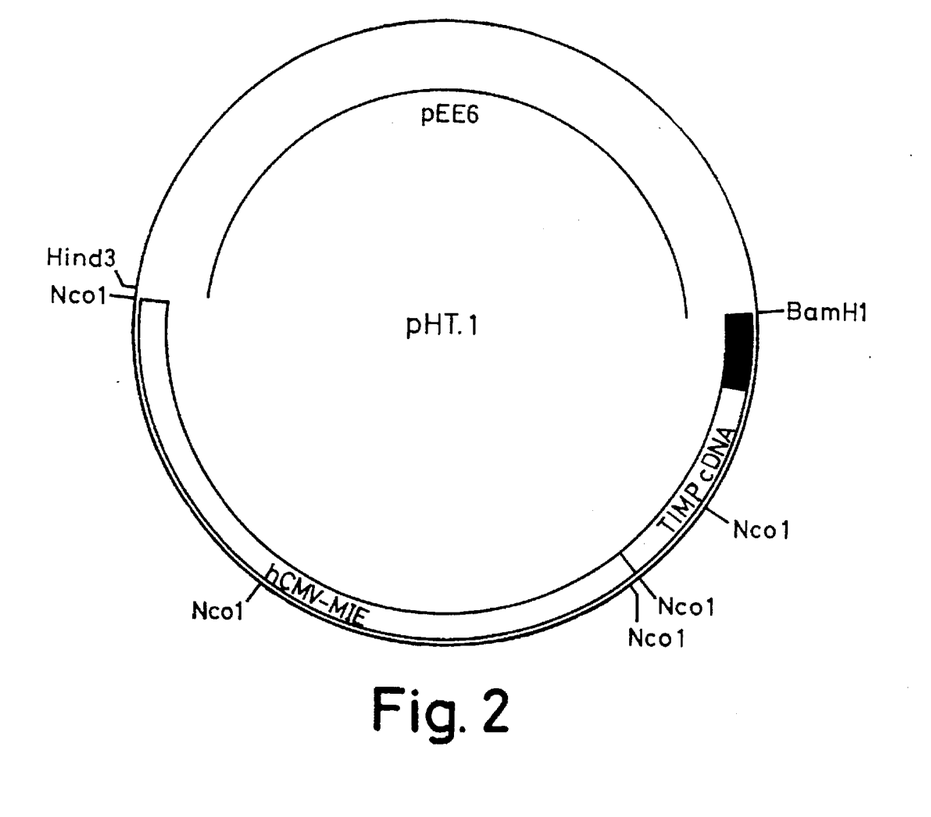
FIG. 2: shows a diagrammatic representation of plasmid pHT.1

The 2129 base-pair NcoI fragment containing the hCMV MIE promoter-enhancer and 5' untranslated sequence was isolated from pCMGS by partial NcoI digestion and inserted at the NcoI site overlapping the translation initiation signal of TIMP in pEE6.TIMP to generate the plasmid pHT.1 (shown in FIG. 2).

Figure 1:
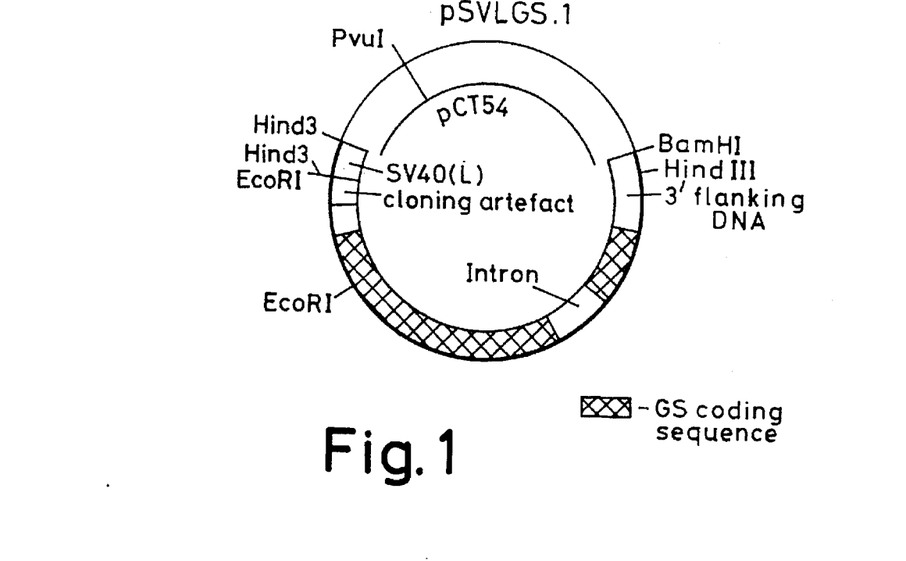
FIG. 1: shows a diagrammatic representation of plasmid pSVLGS.1

A GS gene was introduced into pHT.1 to allow selection of permanent cell lines by introducing the 5.5K PvuI - BamHI fragment of pSVLGS.1 (FIG. 1) at the BamHI site of pHT.1 after addition of a synthetic BamHI linker to PvuI digested pSVLGS.1 to form pHT.1GS. In this plasmid the hCMV-TIMP and GS transcription units transcribe in the same orientation.

pHT.1 GS was introduced into CHO-K1 cells by calcium-phosphate mediated transfection and clones resistant to 20 μM MSX were isolated 2-3 weeks post-transfection. TIMP secretion rates were determined by testing culture supernatants in a specific two site ELISA, based on a sheep anti TIMP polyclonal antibody as a capture antibody, a mouse TIMP monoclonal as the recognition antibody, binding of the monoclonal being revealed using a sheep anti mouse IgG peroxidase conjugate. Purified natural TIMP was used as a standard for calibration of the assay and all curves were linear in the range of 2-20 ng ml$^{-1}$. No non-specific reaction was detectable in CHO-cell conditioned culture media.

One cell line GS.19 was subsequently rationed, and a sub-clone GS 19–12 secretes TIMP at a very high level of $3\times10^8$ molecules/cell/day. Total genomic DNA extracted from this cell line was hybridised with a TIMP probe by Southern blot analysis using standard techniques and shown to contain a single intact copy of the TIMP transcription unit per cell (as well as two re-arranged plasmid bands). This cell line was selected for resistance to higher levels of MSX and in the first selection a pool of cells resistant to 500 μM MSX was isolated and recloned. The clone GS-19.6(500)14 secretes $3\times10^9$ molecules TIMP/cell/day. The vector copy-number in this cell line is approx. 20–30 copies/cell. Subsequent rounds of selection for further gene amplification did not led to increased TIMP secretion.

Thus it appears that the hCMV-TIMP transcription unit from pHT.1 can be very efficiently expressed in CHO-K1 cells at approximately a single copy per cell and a single round of gene amplification leads to secretion rates which are maximal using current methods.

EXAMPLE 3

In order to test whether the hCMV-MIE promoter-enhancer-leader can be used to direct the efficient expression of other protein sequences, two different but related plasminogen activator coding sequences (designated PA-1 and PA-2) were introduced into CHO-K1 cells in vectors in which the protein coding sequences were fused directly to the hCMV-sequence.

In both these cases, there is no NcoI site at the beginning of the translated sequence and so synthetic oligonucleotides were used to recreate the authentic coding sequence from suitable restriction sites within the translated region. The sequence of the modified hCMV translation-initiation signal as used in pBT.1 was also built into the synthetic oligonucleotide which then ended in a Pst-1 restriction site. The Pst-lm fragment of hCMV was then inserted at this site to create the complete promoter-enhancer-leader sequence.

The hCMV-plasminogen activator transcription units were introduced into CHO-K1 cells after inserting a GS gene at the unique BamHI site as above and MSX resistant cell lines secreting plasminogen activator were isolated.

The secretion rates of the best initial transfectant cell lines in each case are given in Table 2. From this it is clear that the hCMV promoter-enhancer leader can also be used to direct the efficient expression of these two plasminogen activator proteins.

TABLE 2

Secretion rates of the different plasminogen activator proteins from transfectant CHO cell lines.

| Plasminogen activator | Molecules secreted/cell/day |
| --- | --- |
| PA-1 | $5.5 \times 10^7$ |
| PA-2 | $1.1 \times 10^8$ |

EXAMPLE 4 pEE6hCMV was made by ligating the Pst-lm fragment of hCMV, HindIII - digested pEE6 and the complementary oligonucleotides of the sequence:

GTCACCGTCCTTGACACGA
|||||||||||||||||
ACGTCAGTGGCAGGAACTGTGCTTCGA cDNA encoding an immunoglobulin light-chain was inserted at the EcoRI site of pEE6.hCMV such that the hCMV-MIE promoter-enhancer leader could direct expression of the cDNA and a selectable marker gene containing the SV40 origin of replication was inserted at the BamHI site of each plasmid.

This plasmid was transfected into COS-1 monkey kidney cells by a standard DEAE-dextran transfection procedure and transient expression was monitored 72 hours post transfection. Light chain was secreted into the medium at at least 100 ng/ml indicating that light chain can indeed be expressed from a transcription unit containing the entire hCMV-MIE 5'-untranslated sequence up to but not including the translation initiation ATG, followed by 15 bases of natural 5'-untranslated sequence of the mouse immunoglobulin light-chain gene.

I claim:

1. A host cell transfected with a recombinant expression vector comprising the promoter, enhancer and complete 5' untranslated region including the first intron of the hCMV-MIE operably linked to a heterologous coding sequence.

2. A process for the recombinant production of a heterologous polypeptide comprising culturing a host cell according to claim 1.

3. A host cell according to claim 1, wherein the recombinant expression vector further comprises a restriction site to facilitate insertion of the heterologous coding sequence.

4. A host cell according to claim 1, wherein the promoter, enhancer and complete 5' untranslated region including the first intron of the hCMV-MIE gene are linked directly to the heterologous coding sequence.

5. A host cell according to claim 1, wherein the recombinant expression vector further includes the translational initiation signal of the hCMV-MIE gene.

6. A host cell according to claim 1, wherein the recombinant expression vector is pCMGS, pEE6.hCMV or pHT.1.

7. A process for the recombinant production of a heterologous polypeptide comprising culturing a host cell according to claim 3.

8. A process for the recombinant production of a heterologous polypeptide comprising culturing a host cell according to claim 4.

9. A process for the recombinant production of a heterologous polypeptide comprising culturing a host cell according to claim 5.

10. A process for the recombinant production of a heterologous polypeptide comprising culturing a host cell according to claim 6.

* * * * *